(12) United States Patent
Neame

(10) Patent No.: US 6,481,436 B1
(45) Date of Patent: Nov. 19, 2002

(54) OBTURATORS AND TUBE ASSEMBLIES

(75) Inventor: Simon Neame, Broadstairs (GB)

(73) Assignee: Smiths Industries Public Limited Company, London (GB)

( * ) Notice: Subject to any disclaimer, the term of this patent is extended or adjusted under 35 U.S.C. 154(b) by 0 days.

(21) Appl. No.: 09/537,085

(22) Filed: Mar. 29, 2000

(30) Foreign Application Priority Data

Apr. 12, 1999 (GB) .............................................. 9908136

(51) Int. Cl.⁷ ............................................ A61M 16/00
(52) U.S. Cl. .............................. 128/200.26; 128/207.14
(58) Field of Search ....................... 604/164.01, 164.1, 604/164.12, 166.01, 170.01, 170.02, 170.03, 264, 523, 525; 606/108; 128/200.26, 207.14–207.17

(56) References Cited

U.S. PATENT DOCUMENTS

| 2,541,402 A | * | 2/1951 | Caine ..................... 128/207.15 |
| 4,909,248 A | * | 3/1990 | Anderson .............. 128/207.14 |
| 5,067,496 A |   | 11/1991 | Eisele |
| 5,222,487 A | * | 6/1993 | Carr et al. ............. 128/200.26 |
| 5,279,610 A | * | 1/1994 | Park et al. ................. 606/108 |
| 5,323,771 A | * | 6/1994 | Fisher et al. ........... 128/200.26 |
| 5,546,937 A |   | 8/1996 | Stuart et al. |
| 5,791,338 A | * | 8/1998 | Merchant et al. ...... 128/200.26 |
| 5,919,183 A | * | 7/1999 | Field ........................... 604/530 |
| 5,937,860 A | * | 8/1999 | Cook ..................... 128/207.15 |

FOREIGN PATENT DOCUMENTS

| EP | 0 371 752 A1 | 11/1989 |
| GB | 2310605 A | 9/1997 |
| GB | 2316321 | 2/1998 |
| GB | 23-163-21 | * 2/1998 ............. 128/200.26 |

* cited by examiner

Primary Examiner—Glenn K. Dawson
(74) Attorney, Agent, or Firm—Connolly Bove Lodge & Hutz LLP

(57) ABSTRACT

An obturator for a tracheostomy tube has a strap extending along its length between a nose at its patient end and a machine end with clips that fasten to a coupling on the tube. The strap has one web extending along its entire length and a second web extending orthogonally on one side of the first web to form a T shape section along the major part of the strap towards its patient end. This makes the patient end of the strap relatively rigid whilst its machine end is relatively flexible to enable the machine end to be twisted to release the engagement of the clips and to enable the obturator to be pulled out of the tube.

14 Claims, 2 Drawing Sheets

OBTURATORS AND TUBE ASSEMBLIES

BACKGROUND OF THE INVENTION

This invention relates to obturators and to tube assemblies.

The invention is more particularly concerned with obturators for use in tracheostomy tubes.

Tracheostomy tubes are often inserted with the aid of an obturator having a pointed end projecting from the patient end of the tracheostomy tube. The tip of the obturator helps separate tissue, enabling smooth entry of the tube. The obturator also helps stiffen the tube and prevents ingress of tissue into the tube, which could cause blockage. Examples of tracheostomy obturators are described in U.S. Pat. Nos. 4,246,897, 5,222,487, GB2224213, GB2316321 and GB2341102. Any displacement of the obturator from its correct position may make insertion of the tube more difficult and, by reducing the smoothness of the patient end of the assembly, may cause trauma to tissue around the stoma. After insertion, the obturator is pulled out of the machine end of the tube. GB 2316321 describes an obturator with a machine end that clips onto the coupling of the tracheostomy tube, the clip being released by twisting it relative to the tube. In this arrangement, the main body of the obturator is a strap of rectangular section so it is relatively flexible to enable twisting. This obturator works well with tracheostomy tubes that are relatively stiff but it does not provide optimal rigidity with more flexible tubes. Although the obturator could be made stiffer to give the desired rigidity for insertion of the tube, this makes it difficult to twist its clip to release engagement with the coupling of the tracheostomy tube.

BRIEF SUMMARY OF THE INVENTION

It is an object of the present invention to provide an alternative obturator and tube assembly.

According to one aspect of the present invention there is provided an obturator for a curved medical tube, the obturator having a patient end shaped with a tapered nose arranged to protrude from the patient end of the tube and a machine end adapted to fasten with the machine end of the tube, the machine end of the obturator being releasable from engagement with the machine end of the tube by twisting relative to the tube, the obturator being substantially rigid along a major part of its length extending from the patient end, and the obturator having a portion of its length adjacent its machine end that is relatively flexible to permit twisting.

The major part of the obturator preferably has two orthogonal webs. The obturator may comprise a first web extending along the length of the obturator from the patient end nose to the machine end and a second orthogonal web extending along only the more rigid part of the obturator. One web may be arranged to extend along substantially in contact with the outside curve of the tube. The obturator is preferably of T shape in section along its major part. The nose of the obturator may have a bore extending through it along its length. The obturator may be a single-piece moulding of a plastics material. The machine end preferably has two resilient arms extending forwardly on opposite sides and adapted to engage the tube. The machine end of the obturator may have a vent hole therein. The obturator is preferably curved along most of its length with a curvature substantially the same as that of the tube.

According to another aspect of the present invention there is provided a tracheostomy tube assembly comprising a tracheostomy tube and an obturator according to the above one aspect of the invention.

The tracheostomy tube is preferably curved with a constant radius along its length.

A tracheostomy tube assembly including an obturator according to the present invention, will now be described, by way of example, with reference to the accompanying drawings.

DETAILED DESCRIPTION OF THE PREFERRED EMBODIMENT

Figure 2:
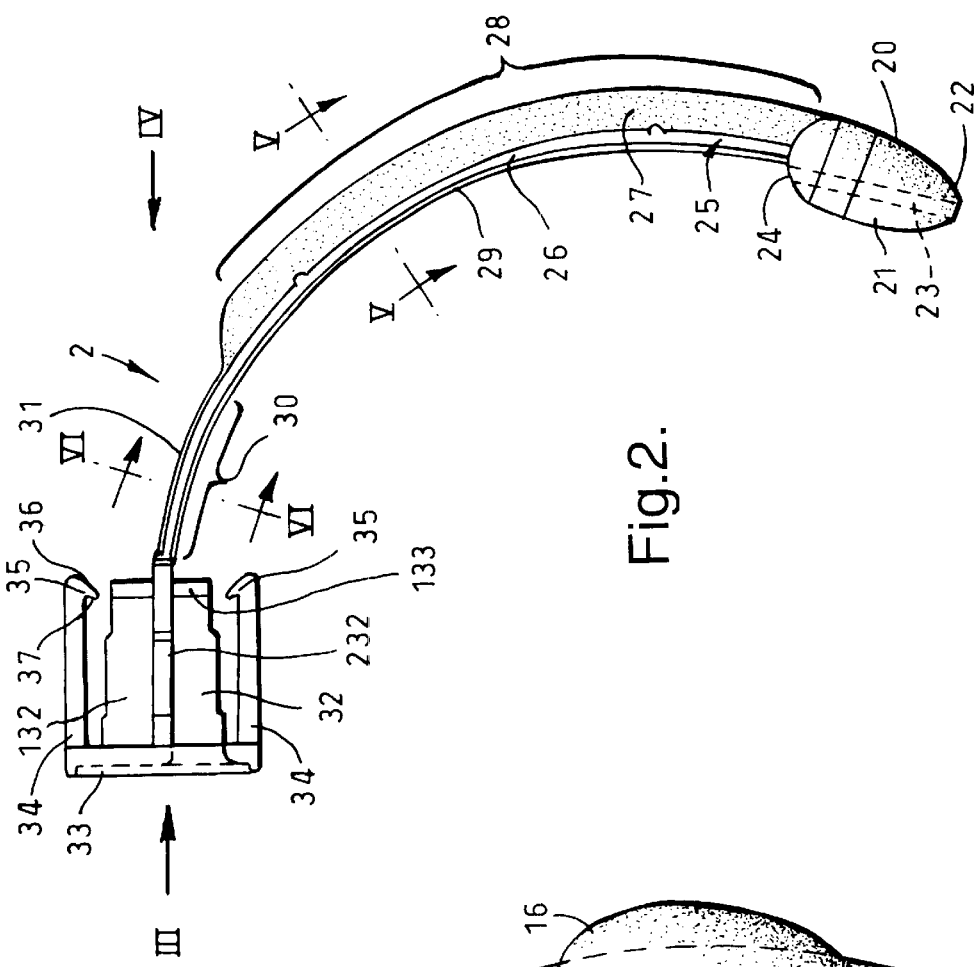
FIG. 2 is a side elevation of the obturator.
Figure 1:
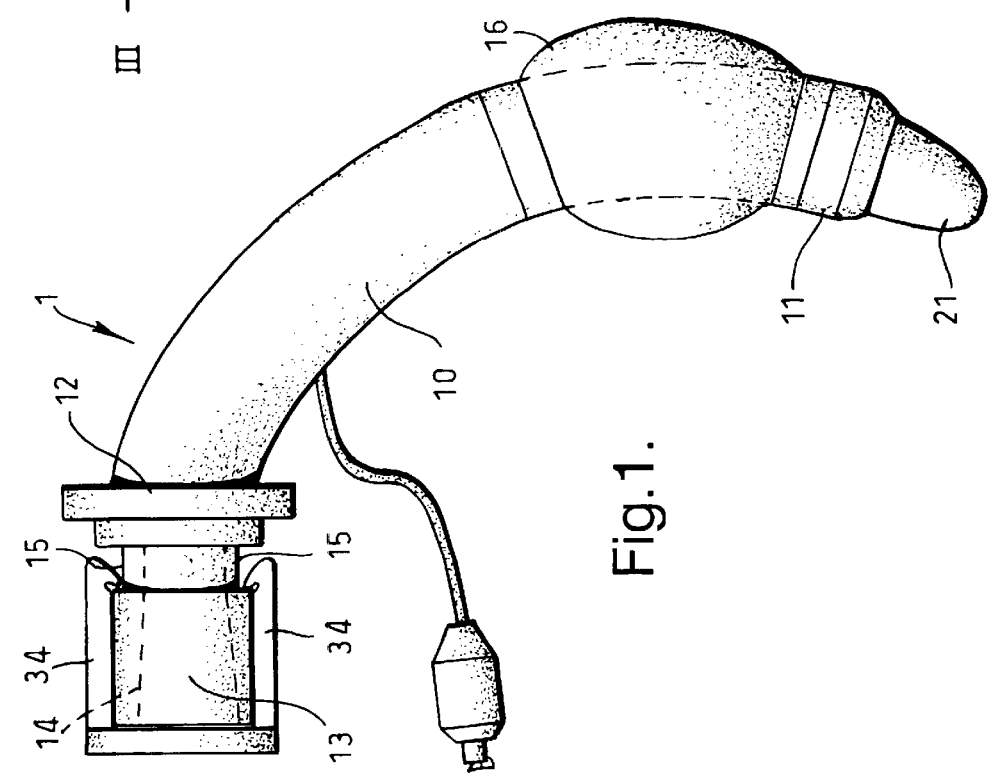
FIG. 1 is a side elevation view of the assembly.
Figure 3:
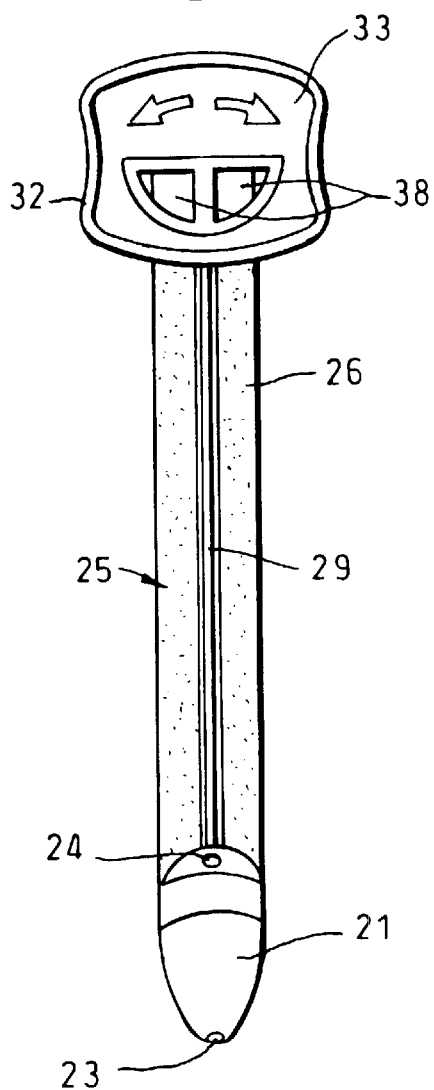
FIG. 3 is an elevation view of the obturator along the line III in FIG. 2.
Figure 4:
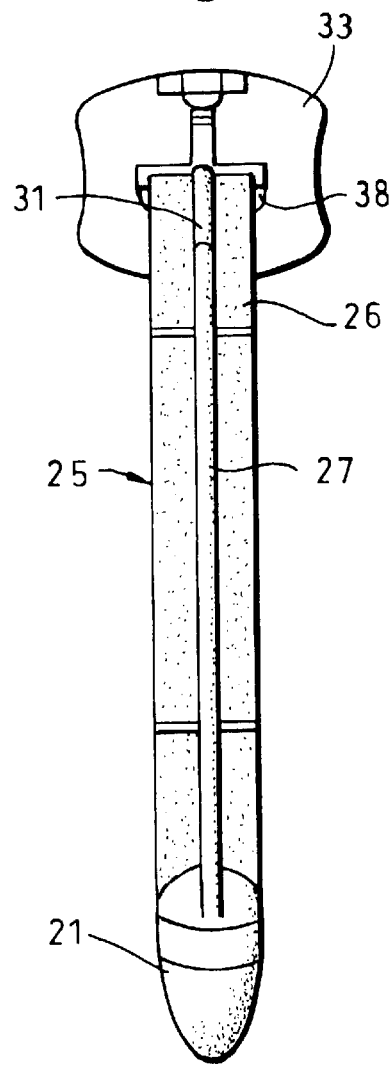
FIG. 4 is an elevation view of the obturator along the line IV in FIG. 2.

The assembly comprises a tracheostomy tube 1 and an obturator 2.

The tube 1 has a conventional shaft 10 of circular section, which is moulded with a curved shape and a constant radius of curvature along its length. The patient end 11 of the shaft 10 is cut square and tapered to be atraumatic. At its machine end, the shaft 10 is moulded integrally with a flange 12 by which the tube can be secured to the patient's neck. The machine end of the shaft 10 is also bonded to a coupling 13 having a female tapered bore 14 shaped to receive a male tapered coupling (not shown) connected to a patient ventilation or anaesthetic circuit. Alternatively, where the patient is breathing spontaneously, the coupling 13 is left open. Externally, the coupling 13 is of cylindrical shape apart from surface formations provided by two, short undercut lips 15 located diametrically opposite one another at the patient end of the coupling. The shaft 10 has an inflatable cuff 16 towards its patient end, for sealing with the inside of the trachea. Alternative tubes need not include such a cuff.

The obturator 2 is a single-piece, integral moulding of a stiff plastics material such as high density polyethylene. At its patient end 20, the obturator 2 has a bullet-shape nose 21, which is a close fit within the patient end 11 of the tube 1. The nose 21 has a tapered tip 22, which, in use, projects from the tube 1 so as to form a pointed continuation of the patient end of the shaft 10. A small diameter bore 23 extends along the nose 21 from its tip 22 to an opening 24 at its rear end.

Figure 5:
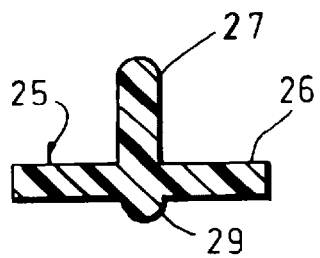
FIG. 5 is a cross-sectional view of the obturator along the line V—V of FIG. 2.
Figure 6:
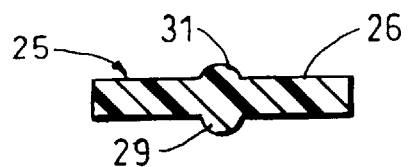
FIG. 6 is a cross-sectional view of the obturator along the line VI—VI of FIG. 2.

Extending rearwardly from the nose 21 the obturator has a curved strap 25 moulded to the curvature of the tube 1. Typically, the strap 25 is about 80 mm long. The strap 25 comprises a web 26 of substantially rectangular section arranged to extend diametrically of the tube shaft 10 as a close sliding fit along its entire length. The strap 25 also has an additional web 27 extending along the major part of the length of the strap, typically along about 60 mm, from the patient end. This additional web 27 extends radially and orthogonally of the first web 26 projecting from one side only towards the outside of its curve so that it substantially contacts the inner wall of the shaft 10 of the tube 1 on the outside of its curvature. The major part 28 of the strap 25 from its patient end therefore has a substantially T-shape in section, as shown in FIG. 5, with just a shallow rib 29 along the side opposite the additional web 27 and is substantially rigid. The machine end 30 of the strap 25 has a substantially rectangular shape in section, as shown in FIG. 6 apart from the rib 29 and a similar shallow rib 31 being a continuation of the additional web 27 and is, therefore, more flexible than the major part 28.

At its machine end 32, the obturator 2 has an enlarged, cruciform section formed by a vertical plate 132 and a horizontal plate 232. The machine end 32 has a tapered exterior, which is a close friction fit within the coupling 13 of the tube 1. A flange 33 extends radially at the machine end of the cruciform section 32 and provides a grip by which the obturator 2 can be inserted and removed from the tube 1. Two resilient arms 34 extend forwardly from the flange 33 on opposite sides of the obturator 2. The arms 34 are terminated at their patient end by surface formations in the form of inwardly-directed catches 35 formed by an inclined ramp 36 and a ledge 37. The dimensions of the arms 34 are such that, when the flange 33 abuts the machine end of the coupling 13, the arms extend along opposite sides of the coupling with the catches 35 engaging under the lips 15, thereby preventing the obturator 2 being removed from the tube. Two vent holes 38 are formed through the flange 33 in alignment with the corners between the cruciform section 32.

In use, the obturator 2 is pushed fully into the tube 1 so that the nose 21 projects from the patient end 11 of the tube and so that the catches 35 engage the lips 15 on the coupling 13, thereby fastening the machine end of the obturator with the machine end of the tube. The assembly is inserted into the patient in the usual way, the obturator 2 providing a tapered lead for the tube into the tracheostomy. The T-shape section along most of the length of the obturator 2 makes it relatively stiff so as to significantly increase the stiffness of the tracheostomy tube 1 and facilitate introduction. Rearward movement of the obturator 2 relative to the tube 1 is prevented by engagement of the catches 35 with the lips 15. Rearward movement of the nose 21 of the obturator 2 within the tube 1 is also resisted by contact of the additional web 27 with the wall of the tube. The patient can breath through the assembly during insertion because of the bore 23 through the nose 21, the passage between the strap 25 and the inside of the tube, and the holes 38 in the flange 33. If desired, a guidewire (not shown) could be threaded through the bore 23 prior to insertion and the assembly slid into position along the guidewire. In order to prevent the rear end of the guidewire catching on the vertical plate 132 when the guidewire is inserted from the patient end of the obturator, the leading edge 133 of the vertical plate is tapered. When the assembly has been inserted to the correct location, the obturator 2 is removed by gripping the flange 33 and twisting it through about 20° so that the catches 35 come out of engagement with the lips 15 and can be pulled rearwardly along the outside of the coupling 13. The flange 33 can be twisted easily despite the stiffness of the patient end of the obturator 2 because the machine end 30 of the obturator is flexible to allow twisting. After removal of the obturator 2, the coupling 13 can be connected to a ventilation circuit or left open, in the usual way.

It will be appreciated that there are alternative twist-releasable arrangements that could be used to fasten the obturator with the tube. The invention could be used with tubes, other than tracheal tubes, where it is necessary to prevent displacement of an obturator relative to a tube.

What I claim is:

1. An obturator for a curved medical tube, the obturator comprising: a patient end shaped with a tapered nose arranged to protrude from a patient end of said tube; a machine end adapted to fasten with a machine end of said tube; said machine end of said obturator being releasable from engagement with said machine end of said tube by twisting relative to said tube; and a strap member extending between said patient end and said machine end of said obturator, wherein said strap member comprises a first region and a second region, said first region extending from said patient end along a major part of the length of the strap member and being substantially rigid, and said second region being adjacent said machine end and being more flexible than said first region to permit twisting of the machine end of said obturator.

2. An obturator according to claim 1, wherein said first region has two orthogonal webs.

3. An obturator according to claim 2, wherein the two webs comprise a first web extending along the length of the strap member from said patient end nose to said machine end and a second orthogonal web extending along only the more rigid part of said strap member.

4. An obturator according to claim 2, wherein one of said webs is arranged to extend along substantially in contact with an outside curve of said tube.

5. An obturator according to claim 1, wherein said strap member is of T shape in section along its said major part.

6. An obturator according to claim 1, wherein the nose of the obturator has a bore extending through it along its length.

7. An obturator according to claim 1, wherein the obturator is a single-piece moulding of a plastics material.

8. An obturator according to claim 1, wherein the said machine end has two resilient arms extending forwardly on opposite sides and adapted to engage said tube.

9. An obturator according to claim 1, wherein the said machine end of said obturator has a vent hole therein.

10. An obturator according to claim 1, wherein the obturator is curved along most of its length with a curvature adapted to be substantially the same as said tube.

11. An obturator according to claim 1, wherein said first region extends about 60 mm from the patient end.

12. An assembly of a tracheostomy tube and obturator, said obturator comprising: a patient end shaped with a tapered nose protruding from a patient end of said tube; a machine end fastened with a machine end of said tube; said machine end of said obturator being releasable from engagement with said machine end of said tube by twisting relative to said tube; and a strap member extending between said patient end and said machine end of said obturator, wherein said strap member comprises a first region and a second region, said first region extending from said patent end along a major part of the length of said strap member and being substantially rigid, and said second region being adjacent said machine end and being more flexible than said first region to permit twisting of the machine end of said obturator.

13. An assembly according to claim 12, wherein said tracheostomy tube is curved with a substantially constant radius of curvature along its length.

14. An assembly according to claim 11, wherein said tracheostomy tube further comprises an inflatable cuff towards its patient end.

* * * * *